(12) United States Patent
Williams et al.

(10) Patent No.: US 8,583,243 B2
(45) Date of Patent: Nov. 12, 2013

(54) APPARATUS FOR STIMULATING AND/OR MONITORING ACTIVITY IN TISSUE

(75) Inventors: Christopher Edward Williams, East Melbourne (AU); Penelope Jayne Allen, East Melbourne (AU); Joel Villalobos Villa, East Melbourne (AU)

(73) Assignee: The Bionics Institute of Australia (AU)

( * ) Notice: Subject to any disclaimer, the term of this patent is extended or adjusted under 35 U.S.C. 154(b) by 0 days.

(21) Appl. No.: 13/392,318

(22) PCT Filed: Aug. 25, 2010

(86) PCT No.: PCT/AU2010/001098
§ 371 (c)(1),
(2), (4) Date: Jun. 8, 2012

(87) PCT Pub. No.: WO2011/022773
PCT Pub. Date: Mar. 3, 2011

(65) Prior Publication Data
US 2012/0245449 A1 Sep. 27, 2012

(30) Foreign Application Priority Data

Aug. 26, 2009 (AU) ................................ 2009904070

(51) Int. Cl.
*A61B 5/04* (2006.01)
*A61N 1/05* (2006.01)
*A61N 1/36* (2006.01)

(52) U.S. Cl.
CPC .......... *A61N 1/36046* (2013.01); *A61N 1/0543* (2013.01)
USPC ............................. 607/54; 600/377; 607/116

(58) Field of Classification Search
USPC ......................................................... 607/54
See application file for complete search history.

(56) References Cited

U.S. PATENT DOCUMENTS

| 4,004,298 | A | * | 1/1977 | Freed | 623/3.1 |
| 4,143,661 | A | * | 3/1979 | LaForge et al. | 607/61 |
| 6,358,281 | B1 | * | 3/2002 | Berrang et al. | 623/10 |
| 6,368,349 | B1 | | 4/2002 | Wyatt et al. | |
| 6,458,157 | B1 | | 10/2002 | Suaning | |
| 2006/0074461 | A1 | | 4/2006 | Tano et al. | |

(Continued)

OTHER PUBLICATIONS

"International Application No. PCT/AU2010/001098, International Search Report and Written Opinion mailed Dec. 22, 2010", 13 pgs.

(Continued)

*Primary Examiner* — Carl H Layno
*Assistant Examiner* — Erin Piateski
(74) *Attorney, Agent, or Firm* — Schwegman Lundberg & Woessner, P.A.

(57) ABSTRACT

A prosthesis is provided comprising a substrate having a distal end and a proximal end; and a plurality of electrodes located at or adjacent the distal end of the substrate. The distal end of the substrate is configured for insertion, via an incision, between first and second tissue layers, such as the sclera and choroid in the eye. The prosthesis tapers in thickness towards the distal end and has a substantially curved provide profile at least on one surface so that the prosthesis can be inserted into position without needing a guide and without causing damage to the tissue or the prosthesis. The prosthesis can include an electrode interface unit located at or adjacent the proximal end of the substrate which locates between the tissue layers. An anchor portion can be provided that extends from the substrate into the incision.

35 Claims, 6 Drawing Sheets

(56) References Cited

U.S. PATENT DOCUMENTS

| | | | |
|---|---|---|---|
| 2007/0049987 A1 | 3/2007 | Greenberg et al. | |
| 2007/0055336 A1* | 3/2007 | Greenberg et al. | 607/141 |
| 2007/0142878 A1* | 6/2007 | Krulevitch et al. | 607/54 |
| 2007/0250135 A1* | 10/2007 | Bartz-Schmidt et al. | 607/54 |
| 2008/0172116 A1* | 7/2008 | Mrva et al. | 607/115 |
| 2009/0069738 A1* | 3/2009 | Rossing et al. | 604/20 |
| 2009/0177245 A1 | 7/2009 | Ameri et al. | |

OTHER PUBLICATIONS

"Poster Session Details", ARVO Conference, Program Number/Board # Range: 3009-3043 / D605-D639; 350; Retinal Prosthesis II; Organizing Section RE, (Apr. 29, 2008), 9 pgs.

Vanhoestenberghe, A., et al., "Hermetic Encapsulation of an Implantable Vision Prosthesis—Combining Implant Fabrication Philosophies", Conference Paper, IFESS 2008, Germany, (2008), 3 pgs.

Wong, Yan Tat, "Effects of Neurostimulation via a Suprachoroidal Vision Prosthesis", University of New South Wales, Graduate School of Biomedical Engineering, Jun. 10, 2009, 162 pgs.

Zhou, J. A., et al., "A Suprachoroidal Electrical Retinal Stimulator Design for Long-Term Animal Experiments and In Vivo Assessment of Its Feasibility and Biocompatibility in Rabbits", Journal of Biomedicine and Biotechnology, vol. 2008, Article ID 547428, 10 pages, Hindawi Publishing Corporation, (2008), 10 pgs.

* cited by examiner

APPARATUS FOR STIMULATING AND/OR MONITORING ACTIVITY IN TISSUE

PRIORITY CLAIM TO RELATED APPLICATIONS

This application is a national stage application under 35 U.S.C. §371 of PCT/AU2010/001098, filed Aug. 25, 2010, and published as WO 2011/022773 A1 on Mar. 3, 2011, which claims priority to Australian Application No. 2009904070, filed Aug. 26, 2009, which applications and publication are incorporated herein by reference and made a part hereof in their entirety, and the benefit of priority of each of which is claimed herein.

FIELD OF THE INVENTION

The present patent application relates to apparatus for stimulating tissue and/or monitoring activity in tissue, particularly, although not necessarily exclusively, an apparatus for stimulating retinal cells of a patient to restore or improve vision.

BACKGROUND

Visual prostheses have been developed to restore vision within blind or partially blind patients. A visual prosthesis commonly includes an implantable component including an electrode array, situated on or in a substrate, for placement in the eye on or near retinal cells. Electrical signals are transmitted via the electrodes to the retinal cells, triggering a perception of light within the patient's brain. The prosthesis can therefore restore vision to patients whose retinal photoreceptors have become dysfunctional.

Commonly, a visual prosthesis is used in conjunction with a video camera. A stream of images detected by the camera is converted into digital signals by an image processor and transmitted in 'real time' to an electrode interface unit. The electrode interface unit is connected to the electrode array via a plurality of conductors and decodes the signals and stimulates the electrodes in accordance with the detected images.

The digital signals can be transmitted wirelessly, at least part or all of the way between the processor and the implantable component. A wireless receiver for receiving the wireless signals can be located on the substrate, or separate to the substrate.

The substrate of the prosthesis can be located in a variety of positions to stimulate the retina. One approach is to place the electrode-carrying part of the substrate between the sclera and the choroid, i.e. into the suprachoroidal space. For example, US 2009/017724525 A1 and US 2006/0074461 A1 each disclose an electrode array placed suprachoroidally, the electrode array being connected via a connecting cable, extending through an incision in the sclera, to an interface unit located to the outside of the sclera (i.e., episclerally). The cable takes the form of a ribbon cable, comprising a plurality of wires connecting individual electrodes to the interface unit.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification the term "visual prosthesis" is used to denote apparatus for restoring or improving a patient's vision, and will be understood to include devices otherwise known as bionic eyes, artificial eyes, retinal prostheses and retinal stimulators or similar.

SUMMARY

According to a first aspect, the present invention provides a visual prosthesis comprising:
a substrate having a distal end and a proximal end;
a plurality of electrodes located at or adjacent the distal end of the substrate; and
an electrode interface unit located at or adjacent the proximal end of the substrate and electrically connected to the electrodes via a plurality of electrical conductors;
wherein the distal end of the substrate is configured for insertion, via an incision in the sclera, to a stimulation position between the sclera and choroid, whereupon the electrode interface unit also locates between the sclera and choroid.

According to a second aspect, the present invention provides a method of implanting a visual prosthesis in an eye, the visual prosthesis comprising: a substrate having a distal end and a proximal end; a plurality of electrodes located at or adjacent the distal end of the substrate; and an electrode interface unit located at or adjacent the proximal end of the substrate and electrically connected to the electrodes via a plurality of electrical conductors, wherein the method comprises:
making an incision in the sclera;
inserting the distal end of the substrate through the incision in the sclera;
locating the distal end of the substrate at or adjacent a stimulation position between the sclera and choroid; and
locating the electrode interface unit between the sclera and choroid.

Prior to locating the distal end of the substrate at or adjacent a stimulation position between the sclera and choroid, preferably a pocket is created between the sclera and choroid, in the suprachoroidal space. The pocket may be created using a tool such as a rounded blade or crescent blade that is inserted through the incision in the sclera before separating the sclera and choroid. The pocket may serve as a predefined space for introducing the distal end of the substrate and may ensure that the substrate remains in the correct anatomical plane between the sclera and choroid as the distal end is advanced to the stimulation position. The depth of the pocket prior to insertion of the substrate may be shorter than the length of the substrate, and the pocket may be lengthened subsequently by the movement of the substrate as it advances into position. The depth of the pocket created prior to insertion of the substrate may be defined by the length of the tool. The substrate may include a depth marker to indicate when the tip of the substrate has reached the end of the pocket created by the tool.

An anchor portion may be connected to the substrate at or adjacent the proximal end of the substrate. The anchor portion can be suitable for anchoring a proximal portion or the proximal end of the substrate in a desired position. The anchor portion can be arranged to locate within the incision in the sclera.

The prosthesis and method of the first and second aspects can have one, some or all of the features of the prosthesis and method respectively, as defined herein with regard to other aspects.

According to a third aspect, the present invention provides a visual prosthesis comprising:

a substrate having a distal end and a proximal end;

a plurality of electrodes located at or adjacent the distal end of the substrate; and an anchor portion connected to the substrate at or adjacent the proximal end of the substrate;

wherein the distal end of the substrate is configured for insertion, via an incision in the sclera, to a stimulation position between the sclera and choroid, whereupon the anchor portion locates in the incision in the sclera.

According to a fourth aspect, the present invention provides a method of implanting a visual prosthesis in an eye, the visual prosthesis comprising: a substrate having a distal end and a proximal end; a plurality of electrodes located at or adjacent the distal end of the substrate; and an anchor portion connected to the substrate at or adjacent the proximal end of the substrate, wherein the method comprises:

making an incision in the sclera;

inserting the distal end of the substrate through the incision in the sclera;

locating the distal end of the substrate at a stimulation position between the sclera and choroid; and locating the anchor portion in the incision in the sclera.

The prosthesis and method of the third and fourth aspects can have one, some or all of the features of the prosthesis and method respectively, as defined herein with regard to other aspects. For example, an electrode interface unit may be located at or adjacent the proximal end of the substrate and electrically connected to the electrodes via a plurality of electrical conductors. However, the electrode interface unit may also be located separately to the substrate, e.g., externally to the eye.

By anchoring the proximal portion or proximal end of the substrate, the proximal portion or end may be fixed in position whilst the remainder, or at least the distal end, of the substrate 'floats' between the sclera and the choroid. One or more sutures can be used to connect the anchor portion to body tissue, e.g., the sclera, at the location of the incision. The suture can be used to both close the incision and connect the anchor portion to the tissue.

The anchor portion may be a projection from the substrate, e.g., a substantially planar element such as a flap of material projecting from the substrate. The projection may be pivotable about its connection with the substrate. The material may be a polymeric material, for example a polyester such as Dacron®. The anchor portion may be a continuous piece of material, or it may be a mesh, and/or comprise one or more cut-out portions. If one or more cut out portions are provided in or near the centre of the anchor portion, the peripheral edges of the anchor portion may provide for anchoring of the substrate, whilst healing of the incision by scleral tissue reconnecting through the cut out sections can take place.

As an alternative, or additionally, the anchor portion may be provided by a cable (i.e., a lead). The cable may serve as a means of electrically communicating with the plurality of electrodes, whilst also providing anchoring function.

The length of the substrate between its proximal and distal ends may be chosen to achieve the desired insertion arrangement, depending on the position at which the incision is made in the sclera relative to the intended stimulation position. The length may be 18 to 28 mm, for example. The incision in the sclera can be towards the front of the eye, e.g., about 4 mm to 8 mm, e.g., 5 mm, behind the limbus. This position may provide for relatively easy surgical access, wound repair and access to a space between the sclera and choroid sufficiently recessed from the stimulation position to fit the electrode interface unit. The anchor portion can be connected to the substrate at about 12 mm to 28 mm from the distal end tip of the substrate, e.g., at 20 or 26 mm from the distal end tip. The electrodes may be located within a region of the substrate extending about 5 mm to 20 mm from the distal end tip. The substrate may be about 5 to 14 mm wide.

The anchor portion may be connected at a position spaced inwards from the proximal end, leaving a lip of the substrate to extend proximally from the anchor portion to a proximal end edge. The lip can project to the opposite side of the connection with the anchor portion to that of the distal end of the substrate. The lip may be 1 to 3 mm long, for example. By having a portion of the substrate extending proximally from the connection with the anchor portion, the substrate and anchor portion can seat relatively more stably against scleral tissue at the incision region. The portion may provide, in essence, a stabilizing tail to the substrate, and may support tissue around the incision and minimise the risk of leakage and choroidal incarceration.

In any of the aspects described herein, insertion of the substrate may be carried out using forceps, such as soft-tipped forceps to prevent damage. The substrate may be inserted to a point where the tip is between about 2 mm and 4 mm from the optic disc (head of the optic nerve). To assist in achieving the desired insertion depth, depth insertion markers may be placed on the substrate. One or more different depth markers may be provided to address different eye sizes and/or different incision points in the sclera. To prevent the substrate from being inserted back-to-front, or the wrong way round, the substrate may also or instead include left and right side indicators, outside and inside indicators and/or a distal tip indicator. The distal tip indicator may be an arrow or other indicia indicative of the direction in which the substrate is to be inserted into the incision. After the insertion of the substrate, the incision may be closed, e.g., using sutures such as dissolving or non-dissolving sutures.

The plurality of conductors connecting the electrodes and the interface unit, whether the interface is located in the substrate or elsewhere, may take the form of electrically conducting wires, such as metal wires, e.g., platinum wires. The conductors can be electrically insulated from one another, and/or electrically insulated from surrounding eye tissue at least partially along their length. At or adjacent the distal end of the substrate, electrical insulation may be omitted in order to form the electrodes. However, other types of electrodes such as disk electrodes with e.g., 0.2 to 0.8 mm diameter may be used. The conductors can extend within the substrate. The conductors can take the form in combination with the substrate of a ribbon cable. Alternatively, the conductors may take the form of one or more coiled wires. The coiled wires may be located within a conduit in the substrate or in a sheath as part of a cable external to substrate. The cable extending from the substrate, including the sheath, may be coiled. By using coiled wire and cable, the wire and cable may be stretchable, allowing for stretching as the substrate flexes or the cable flexes, e.g., during insertion of the substrate in the eye or during subsequent use of the implanted substrate, e.g., when the eye rotates. Other types of stretchable wire or cable may be used, such as twisted, curved or zig zag wires or cables.

The plurality of conductors can terminate at the electrode interface unit, meaning that there is no requirement for these conductors to exit the sclera if the electrode interface unit is located in or on the substrate. In essence, the substrate can be configured to be sealed entirely within the bounds of the sclera. Signals generated outside the eye, such as signals for stimulating the electrodes, may be transmitted to the interface unit of the substrate via a relatively small cable (this can be a cable with a non-flat configuration (a 'round cable'), such as a cable with a substantially circular cross-section) or wirelessly. If wireless transmission is used, the point of incision in the sclera may be closed completely, or, if a round cable is used, to a greater degree than if a ribbon cable (e.g. the substrate itself) were to extend out of the incision. In this regard, the likelihood of scleral lesions or choroid rupture is relatively reduced compared to arrangements which rely on use of a ribbon cable extending through the location of the incision.

The incision in the sclera and adjacent region between the sclera and choroid may provide a particularly compliant region and/or large open space for locating the anchor portion and electrode interface unit. The proximal portion of the substrate may have a relatively wider configuration than a distal portion of the substrate, enabling a relatively larger interface unit or more than one interface unit to be located in the substrate. In this regard, the substrate may take a "T" shape or an "L" shape. The choroid provides a natural heat sink for the components of the interface unit, providing effective heat dissipation and improving component performance.

In any of the aspects described herein, the incision may be straight, curved or angular at its opening on the surface of the sclera. For example, particularly to enable accommodation of a cable or lead extending from the substrate, the incision may take an "L" shape, formed from two substantially straight cuts extending perpendicularly to each other. The substrate may be inserted through one of the cuts and, during or after insertion, the cable may extend out of the incision via the other of the cuts.

The distal portion of the substrate and the electrodes thereon may be configured for stimulating retinal cells. Further, the stimulation need not stimulate only a central region of the patient's vision, but also peripheral regions of the patient's vision. To achieve this, the electrodes may be spread over a relatively large area of the substrate.

During implantation of the prosthesis, the distal end of the substrate may be pushed into position between the sclera and choroid without using a guide.

According to a fifth aspect, the present invention provides a visual prosthesis comprising:
 a substrate having a distal end and a proximal end; and
 a plurality of electrodes located at or adjacent the distal end of the substrate
 wherein the distal end of the substrate is configured for insertion, via an incision in the sclera, to a stimulation position between the sclera and choroid, without using a guide.

According to a sixth aspect, the present invention provides a method of implanting a visual prosthesis in an eye, the visual prosthesis comprising: a substrate having a distal end and a proximal end; and a plurality of electrodes located at or adjacent the distal end of the substrate; wherein the method comprises:
 making an incision in the sclera;
 inserting the distal end of the substrate through the incision in the sclera; and
 locating the distal end at a stimulation position between the sclera and choroid without using a guide.

In any of the above aspects, by not using a guide (such as a guide wire), during the insertion process, only the prosthesis need be inserted between the sclera and choroid, or only the prosthesis need be inserted through the incision in the sclera and between the sclera and choroid. Steering of the prosthesis to the stimulation position may be through use of the forceps to the outside of the incision only. So that a guide need not be used, an appropriate stiffness for the substrate may be chosen. The substrate can be stiff enough to be pushed into position without buckling (e.g., rolling), yet flexible enough to conform to the anatomy of the sclera and choroid. When a guide is not used, insertion of the prosthesis may be simplified and the chances of damaging eye tissue during insertion may be reduced.

The prosthesis and method of the fifth and sixth aspects can have one, some or all of the features of the prosthesis and method respectively, as defined herein with regard to other aspects.

According to a seventh aspect, the present invention provides a visual prosthesis comprising:
 a substrate having a distal end and a proximal end; and
 a plurality of electrodes located at or adjacent the distal end of the substrate;
 wherein the distal end of the substrate is configured for insertion, via an incision in the sclera, to a stimulation position between the sclera and choroid, the distal end of the substrate being stiff enough to be pushed into position without buckling, yet flexible enough to at least substantially conform to the anatomy of the sclera and choroid.

According to an eighth aspect, the present invention provides a method of implanting a visual prosthesis in an eye, the visual prosthesis comprising: a substrate having a distal end and a proximal end; and a plurality of electrodes located at or adjacent the distal end of the substrate for stimulating the retina, wherein the method comprises:
 making an incision in the sclera;
 inserting the distal end of the substrate through the incision in the sclera; and
 locating the distal end at a stimulation position between the sclera and choroid,
 wherein the distal end of the substrate is stiff enough to be pushed into position without buckling, yet flexible enough to at least substantially conform to the anatomy of the sclera and choroid.

The prosthesis and method of the seventh and eighth aspects can have one, some or all of the features of the prosthesis and method respectively, as defined herein with regard to other aspects.

In any of the aspects, to realise a substrate with the desired stiffness and flexibility, an appropriate material and/or thickness and/or surface profile of the substrate may be chosen. The material may be a flexible polymer, such as polyimide. The substrate may taper toward the distal end, permitting relatively greater flexing at the distal end region.

According to a ninth aspect, the present invention provides a visual prosthesis comprising:
 a substrate having a distal end, a proximal end; and top and bottom surfaces extending between the distal end and proximal end, and
 a plurality of electrodes located at or adjacent the distal end of the substrate;
 wherein the distal end of the substrate is configured for insertion, via an incision, to a stimulation position between the sclera and choroid; and
 wherein the thickness of the substrate between the top and bottom surfaces tapers toward the distal end of the substrate.

In any of the aspects, to provide the tapering, one or both of the top and bottom surfaces of the substrate may have a substantially curved profile between the proximal and distal ends, i.e., in the longitudinal direction of the substrate. When only one of the top and bottom surfaces of the substrate has a substantially curved profile between the proximal and distal ends, the other of the top and bottom surfaces may be substantially flat. For example, the top surface, which may be for locating adjacent the sclera, may have a curved profile in the longitudinal direction of the substrate, whereas the bottom surface, which may be for locating adjacent the choroid, may be substantially flat. Although the thickness of the substrate may taper toward the distal end, the width of the substrate may be substantially uniform at least throughout this tapering portion. The substrate may taper from a thickness of 0.8 mm to 0.15 mm, for example.

The thickest part of the substrate may be at or adjacent the proximal end of the substrate. The thickest part of the substrate may be at an intermediate position between the proximal and distal ends. When the thickest part is at an intermediate position between the proximal and distal ends, the thickness of the substrate may also taper towards the proximal end. Nonetheless, the thickest part of the substrate may be nearer to the proximal end than the distal end, which may mean that maximum flexibility is provided at the distal end rather than the proximal end of the substrate.

The substrate may taper in thickness towards each side of the substrate, from a central region of the substrate, in the lateral direction of the substrate. One or both of the top and bottom surfaces of the substrate may have a substantially curved profile between the sides of the substrate, i.e. in the lateral direction of the substrate. The profile of the top and/or bottom of the substrate may be part-spherical in the lateral direction, for example. This may ensure that the substrate conforms to the shape of the choroid and/or sclera to improve ease of insertion and to ensure that the substrate fits neatly between the tissue layers.

The prosthesis of the ninth aspect can have one, some or all of the features of the prosthesis as defined herein with regard to other aspects.

In any of the aspects, the substrate may have a composite construction with a relatively stiffer core region and a relatively softer outer region. For example, the substrate may comprise one or more longitudinally extending ribs or spines to maintain the desired stiffness in the insertion direction to prevent buckling, whilst permitting the substrate to bend laterally to the contours of the sclera and choroid.

According to a tenth aspect, the present invention provides a visual prosthesis comprising:
 a substrate having a distal end and a proximal end; and
 a plurality of electrodes located at or adjacent the distal end of the substrate; and
 one or more ribs or spines provided in or on the substrate and extending some or all of the distance between the proximal and distal ends of the substrate;
 wherein the distal end of the substrate is configured for insertion, via an incision in the sclera, to a stimulation position between the sclera and choroid.

In any of the aspects, the one or more ribs or spines may extend parallel or at an angle to the longitudinal axis of the substrate and may be located centrally or offset from centre, in the lateral direction of the substrate. Where more than one rib or spine is provided, they are preferably spaced apart in the lateral direction of the substrate. The ribs or spines may be located on the top or bottom surface, or between the top and bottom surface, of the substrate and may be formed of a different material to a surrounding portion of the substrate, e.g. formed of a relatively more dense material. The ribs or spines may be formed integrally with the rest of the substrate, or may be inserted into the substrate and may be of silicone or polyimide. In one embodiment, the electrical conductors connected between the electrodes and interface unit may be bundled together to form one or more ribs or spines, and in another embodiment slots may be disposed in the substrate for increased flexibility.

Further, in any of the aspects described herein, to enable the substrate to flex laterally, when an electrode interface unit is comprised in the substrate, the electrode interface unit may be divided into two or more sections, spaced apart laterally, at or adjacent the proximal end of the substrate. The proximal portion of the substrate may therefore bend about a central region between the two sections of the interface unit. In general, components of the visual prosthesis embedded or located in or on the substrate may be spaced apart, with zones of relatively high flexibility being located between these components to enable the substrate to conform at least substantially to the contours of the sclera and choroid. A relatively soft, conformable and biocompatible coating (e.g. silicone or polyurethane) may be applied to the substrate over these zones, or indeed over the entirety or other areas of the substrate. Additionally or alternatively, the substrate may be preformed to at least substantially follow the contours of the sclera and choroid, and/or the substrate may be formed such that it is biased to take up a configuration, upon insertion, that at least substantially follows the contours of the sclera and choroid, e.g. take up a substantially part-spherical shape as discussed in preceding aspects.

The prosthesis and method of the tenth aspect can have one, some or all of the features of the prosthesis and method respectively, as defined herein with regard to other aspects.

In any of the above aspects, to prevent damage to the sclera, choroid, or the optic disc upon insertion, the distal tip of the substrate at its distal portion may be relatively thin in comparison to the rest of the substrate and/or may take a rounded form. A bumper may be located at the tip and/or lateral edges of the substrate, which bumper may be formed from the same or a different material to the rest of the substrate. The bumper may be a portion of relatively thin, soft and/or smooth material projecting from the edges of the substrate. The bumper may be silicone or polyurethane and the remainder of the substrate may be polyimide, for example. The bumper may be flexible yet provide an antiroll tip to the distal end edge of the substrate and may be 0.5 to 3 mm long, for example.

The visual prosthesis of any of the above aspects may be comprised in vision restoration apparatus, the apparatus comprising, additionally:
 an image receiver for receiving a stream of images;
 an image processor for converting the stream of images received by the image receiver into electrical signals;
 a wireless transmitter connected to the image processor for transmitting the electrical signals wirelessly; and/or
 a wireless receiver connected to the electrode interface unit for receiving the electrical signals from the wireless transmitter.

The image receiver may be a video camera and may be located on eyeglass frames. The wireless receiver may be positioned with the electrode interface unit at or adjacent the proximal end of the substrate, and thus may be located entirely within the eye, e.g., between the sclera and the choroid. Alternatively, the wireless receiver may be located outside the eye and may be connected to the electrodes via a cable that exits the eye, e.g., through an incision in the sclera. The wireless receiver may be positioned on the surface of the eye or on the skull at the side or rear of the patient's head.

The cable may be stabilised at the scleral incision exit to minimise flexing, preventing damage to the surrounding tissue. Stabilisation may be achieved using one or more anchors. One or more of the anchors may comprise Dacron® and/or silicone material, and may be formed at least in part as a mesh, e.g., an open Dacron® mesh. One or more of the anchors may take the form of a patch. The anchors may extend over the cable and may be fixed at their sides to the outer surface of the sclera (and/or other parts of the user's head as the cable extends to the wireless receiver). The anchor may be adhered to the cable and/or fixed either side of the cable using sutures, e.g., Nylon 8.0 sutures. The anchor may be coated, e.g., Parylene coated, e.g., with silicone, to avoid unwanted adhesion between the anchor and body tissue. The cable may be a helical lead with high flex properties. This may permit it to flex as the eye is rotated, without causing damage to tissue at its exit point from the sclera. The anchors may be positioned strategically to prevent any obstruction to the extraocular muscles that cause the eye to rotate. Preferably at least one anchor (e.g., a scleral patch) is located on the surface of the sclera close to, or over, the incision to support the cable as it exits the incision.

According to one aspect of the invention, there is provided a scleral patch in combination with a visual prosthesis according to any one of the preceding aspects.

The scleral patch may force a change in direction of extension of the cable. For example, the patch may fix a bend in the cable, the bend being such that the cable extends in a desirable direction as it travels further from the incision. Preferably the patch is glued to the cable to provide stress relief for the highly movable cable. The patch may comprise silicone such as reinforced silicone. The patch may be connected to the cable during insertion of the substrate in the eye.

The electrode interface unit may decode the electrical signals and convert the signals into a plurality of individual signals for transmitting to each electrode. The electrode interface unit may comprise one of more switching circuits, e.g., cross point switch matrices, to allow communication with each electrode. There can be 30 electrodes or more, although any number of electrodes may be used. In one embodiment, 98 electrodes are provided. Preferably, when the electrode interface unit is comprised in or on the substrate, the electrode interface unit is hermetically sealed, e.g., to protect electronic components of the electrode interface unit from damage by body fluids and/or to protect the patient from exposure to chemicals contained in electronic components of the electrode interface unit. One or more electrically conductive feed through portions may be located on a wall of a casing of the electrode interface unit, the feed through portions being connected to the electrical conductors and allowing electrical communication between electrical components located within the casing and the plurality of electrodes, whilst ensuring that the casing is hermetically sealed.

It is envisaged that the visual prosthesis as described in any one of the aspects above could be adapted as a device for tissue stimulation, or the sensing of electrical activity in tissue, in others areas of the body. In essence, instead of the tissue layers being the sclera and choroid of the eye, the tissue layers may be any directly adjacent tissue layers of the body at a point where tissue stimulation or the sensing of electrical activity in tissue is to be carried out.

According to an eleventh aspect, the present invention provides a tissue stimulation or sensing device comprising:

a substrate having a distal end and a proximal end, a plurality of electrodes located at or adjacent the distal end of the substrate for stimulating tissue or sensing electrical activity in the tissue, an electrode interface unit located at or adjacent the proximal end of the substrate and electrically connected to the electrodes via a plurality of electrical conductors;

wherein the distal end of the substrate is configured for insertion, via an incision in a first tissue layer, to a stimulation or sensing position between the first tissue layer and a second tissue layer directly adjacent to the first tissue layer, whereupon the electrode interface unit also locates between the first and second tissue layers.

According to a twelfth aspect, the present invention provides a method of implanting a tissue stimulation or sensing device in tissue, the device comprising: a substrate having a distal end and a proximal end; a plurality of electrodes located at or adjacent the distal end of the substrate for stimulating or sensing electrical activity in tissue, and an electrode interface unit located at or adjacent the proximal end of the substrate and connected to the electrodes via a plurality of electrical conductors, wherein the method comprises:

making an incision in a first tissue layer;

inserting the distal end of the substrate through the incision in the first tissue layer;

locating the distal end at a stimulation or sensing position between the first tissue layer and a second tissue layer directly adjacent to the first tissue layer; and locating the electrode interface unit between the first and second tissue layers.

According to a thirteenth aspect, the present invention provides a tissue stimulation or sensing device comprising:

a substrate having a distal end and a proximal end;

a plurality of electrodes located at or adjacent the distal end of the substrate for stimulating tissue or sensing electrical activity in the tissue; and an anchor portion connected to the substrate at or adjacent the proximal end of the substrate;

wherein the distal end of the substrate is configured for insertion, via an incision in a first tissue layer, to a stimulation position between the first tissue layer and a second tissue layer, whereupon the anchor portion locates in the incision in the first tissue layer.

According to a fourteenth aspect, the present invention provides a method of implanting a tissue stimulation or sensing device in tissue, the device comprising: a substrate having a distal end and a proximal end; a plurality of electrodes located at or adjacent the distal end of the substrate for stimulating tissue or sensing electrical activity in the tissue; and an anchor portion connected to the substrate at or adjacent the proximal end of the substrate, wherein the method comprises:

making an incision in a first tissue layer;

inserting the distal end of the substrate through the incision in the first tissue layer;

locating the distal end at a stimulation or sensing position between the first tissue layer and a second tissue layer; and locating the anchor portion in the incision in the first tissue layer.

According to a fifteenth aspect, the present invention provides a tissue stimulation or sensing device comprising:

a substrate having a distal end, proximal end; top and bottom surfaces extending between the distal end and proximal end, and a plurality of electrodes located in or on the substrate;

wherein the distal end of the substrate is configured for insertion, via an incision in the first tissue layer, to a stimulation position between the first and second tissue layers; and wherein the thickness of the substrate between the top and bottom surfaces tapers towards the distal end of the substrate.

According to a sixteenth aspect, the present invention provides a tissue stimulation or sensing device comprising:

a substrate having a distal end and a proximal end;

a plurality of electrodes located in or on the substrate for stimulating tissue or sensing electrical activity in the tissue; and one or more ribs or spines provided in or on the substrate and extending some or all of the distance between the proximal and distal ends of the substrate, wherein at least a portion of the substrate is configured for insertion, via an incision, to a stimulation position between first and second tissue layers.

The first and second tissue layers may be layers within the eye, e.g., the sclera and choroid, or layers other than one or both of the sclera and choroid, e.g., the layers may be the retina and choroid. The device may therefore be for episcleral, subretinal or epiretinal use. Alternatively, the tissue layers may be layers in other parts of the body, such as tissue layers surrounding the brain, e.g. the dura. The device may be used in Electroencephalography (EEG) techniques, where electrical activity within the brain is monitored. The device may be used in subdural EEG (sdEEG), with the first tissue layer being the dura. The second tissue layer may be the arachnoid and thus the substrate may locate in the duraarachnoid interface region. Alternatively, the substrate may be arranged to locate in the epidural space adjacent the spinal cord. Notably, the dura has a similar biological function to the sclera, discussed with respect to previous aspects. The device can have applications in cortical EEG, as a seizure monitor and stimulator. The device may be used in brain and spinal cord stimulation or monitoring, e.g. to monitor seizure activity and/or to block or prevent seizures and may utilize temporal lobe electrodes. Spinal cord stimulation may be used to treat some pain syndromes. The device may be used in cardiology, and may located under the pericardium for example. Depending on where the device is used, electrodes may be positioned at different regions of the substrate, such as a central region of the substrate or even at or adjacent the proximal end of the substrate.

The device of any of the eleventh to sixteenth aspects may comprise any one or more of the features described herein with respect to other aspects.

BRIEF DESCRIPTION OF THE DRAWINGS

By way of example only, embodiments are now described with reference to the accompanying drawings, in which:

FIG. 3 shows an example electrode and wire topography for the prosthesis of FIG. 1a;

FIG. 10a shows a top view of a visual prosthesis according to a third embodiment, FIGS. 10b and 10c show cross-sectional views of the perimeter of the prosthesis of FIG. 10a along lines A-A and B-B of FIG. 10a respectively; and FIG. 10d shows a top view of a bottom layer of the prosthesis of FIG. 10a;

DETAILED DESCRIPTION EMBODIMENTS

Figure 1A:
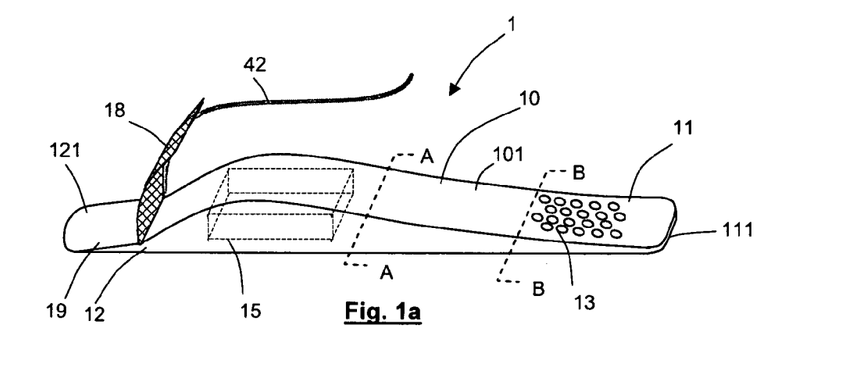
FIG. 1a shows an oblique side view of a visual prosthesis according to a first embodiment.
Figure 3:
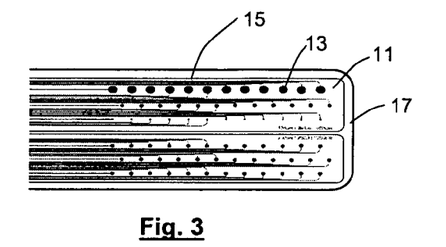

A visual prosthesis 1 according to a first embodiment is shown in FIG. 1a. The prosthesis 1 comprises an implantable component comprising a substrate 10 having a distal end 11 and a proximal end 12. The substrate 10, when viewed from above, is substantially rectangular, with curved corners, its longitudinal direction extending between the distal and proximal ends 11, 12. Adjacent the distal end 12 of the substrate 10, an array of electrodes 13 is provided for stimulating retinal cells of an eye. Each electrode is connected via a separate electrical conductor, e.g., a biocompatible metal wire 14 such as a platinum wire, to an electrode interface unit 15. The conductors 14 are electrically insulated from one another and electrically insulated from surrounding eye tissue as they extend from the electrode interface unit to the electrodes. The electrode interface unit is depicted embedded in the substrate 10 at the proximal end 12. The electrode interface unit 15 is hermetically sealed to protect electronic components of the electrode interface unit 15 from damage by body fluids and to protect the patient from exposure to chemicals contained in the electronic components. An example electrode and wire topography for the substrate is shown in FIG. 3. Flexible/photolithographic or lasered wiring and array fabrication can be employed in the construction of the device. The embodiment of the electrode interface unit 15 that is depicted comprises a cross-point switch matrix to enable communication with each electrode individually.

Figure 2:
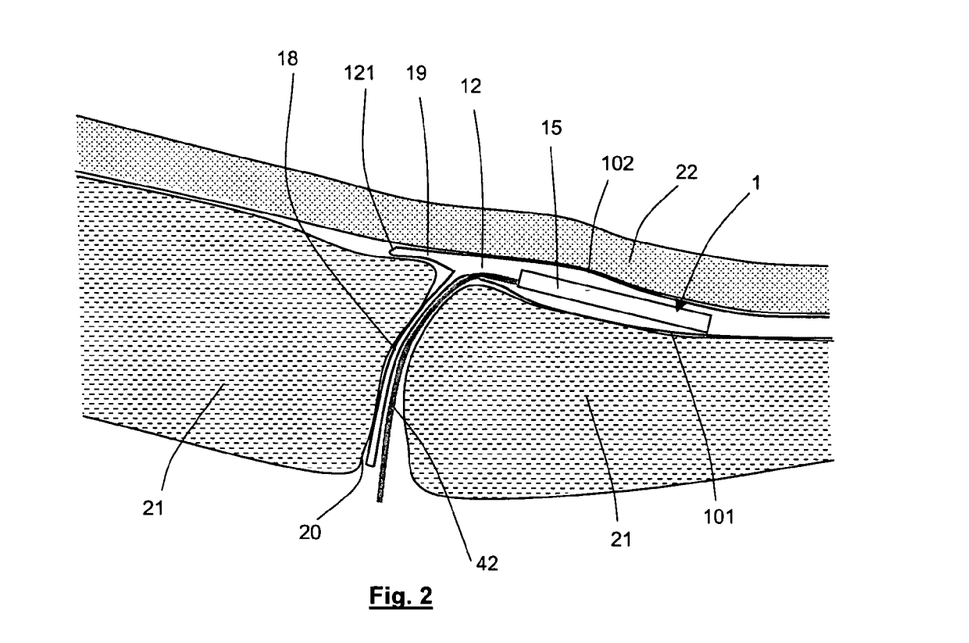
FIG. 2 shows a cross-sectional side view of the prosthesis of FIG. 1a when located between the sclera and choroid.

Referring to FIG. 2, the prosthesis 1 is arranged to be implanted at least partially between the sclera 21 and the choroid 22 layers of the eye, via an incision 20 in the sclera 21.

Figures 4A, 4B, 4C:
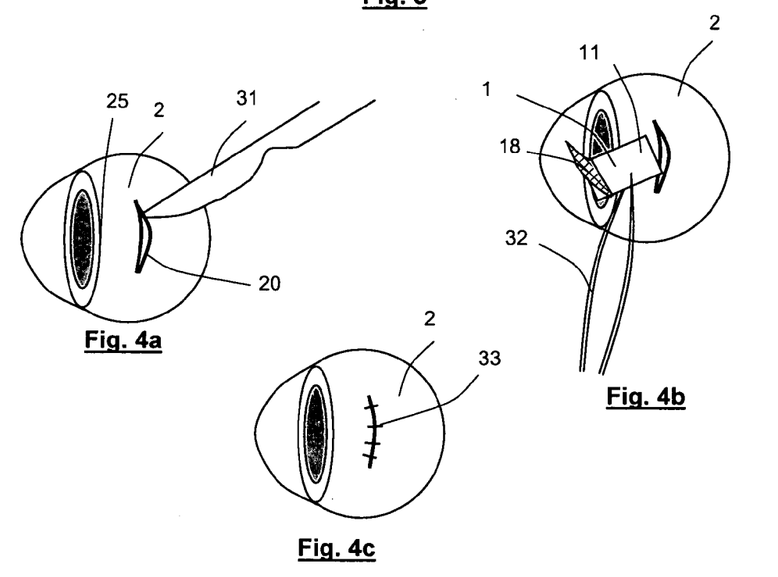
FIGS. 4a to 4c represent steps that can be carried out to implant the prosthesis of FIG. 1a in an eye.

The implantation steps according to one embodiment of the invention are represented in FIGS. 4a to 4c. An incision 20 is made in the sclera with a scalpel 31, the incision 20 being slightly wider than the width of the substrate 10 (FIG. 4a), and then the distal end 11 of the substrate 10 is pushed into the incision, using soft-tipped forceps 32; through the scleral layer and into a pocket between the sclera and the choroid (FIG. 4b). Once fully inserted, the opening of the incision is closed using sutures 33 (FIG. 4c). In this embodiment, the incision 20 is about 5 mm from the corneal limbus 25.

Referring again to FIGS. 1a to 1c and FIG. 2, the substrate 10 is thickest at or near the proximal end 12 and tapers in thickness toward the distal end 11. (In this embodiment, the substrate 10 tapers from a maximum thickness of about 1 mm to a minimum thickness of about 0.15 mm). The resulting wedge shape is well suited to gradually opening up the pocket (cleavage plane) between the sclera 21 and the choroid 22 as the distal end 11 is pushed into position, creating space for the thicker proximal end 12 where the relatively large electrode interface unit 15 is located. Since the substrate 10 tapers toward the distal end 11, the distal end is relatively flexible, enabling it to conform to the anatomy of the sclera and choroid layers as it is pushed into place. Nevertheless, to prevent buckling as it is pushed forward, a central spine 16 is provided in a core region of the substrate 10.

Figure 1B:
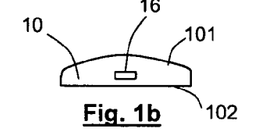
FIGS. 1b and 1c show cross-sectional views of the prosthesis of FIG. 1a along lines A-A and B-B of FIG. 1a respectively.
Figure 1C:
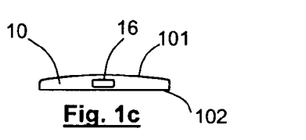

The central spine 16 is an elongate portion embedded in the substrate between the top surface 101 and bottom surface 102 of the substrate 10. The spine 16 extends parallel to the longitudinal direction of the substrate and is located centrally in the lateral direction of the substrate. The central spine is of stiffer material than the surrounding substrate and it therefore stiffens the substrate 10, particularly in the longitudinal direction, but permits enough flexing of the substrate 10, particularly in the lateral direction (the direction across the width of the substrate), to allow the substrate to at least substantially if not wholly conform to the sclera 21 and choroid 22. The controlled flexibility and stiffness of the substrate 10 enables the substrate 10 to be pushed into position without introducing a guide into the incision 20. In alternative embodiments, the wires 14 connecting the electrodes 13 to the electrode interface unit 15 are bundled together to create one or more spines, and in other embodiments, ribs on and/or cuts in the substrate 10 are provided. With reference to FIGS. 1b and 1c, although the spine 16 is present in both the relatively thick proximal end region of the substrate 10 (which can have a thickness of about 1 to 1.2 mm for example) and the relatively thin distal end region of the substrate 10 (which can have a thickness of about 0.3 to 1 mm for example), in alternative embodiments the spine 16 may be present at the relatively thin distal end region only, for example. In this regard, the relatively thick proximal end region of the substrate 10 may have sufficient stiffness to prevent buckling at that region without the spine 16 being present. If the substrate 10 comprises silicone, for example, it may exhibit sufficient stiffness at the proximal region of the substrate 10 without needing a spine 16.

By having relatively flexible distal end 11, the risk of damage to the eye tissue, e.g. the optic disc, upon insertion of the substrate 10 may be reduced. Nonetheless, to provide additional protection against damage, the prosthesis in this embodiment comprises a bumper 17 that projects from the outer edge of the substrate 10 (see FIG. 3). The bumper 17 is a portion of relatively thin, soft, compliant material, with curved corners, that can deform when contact with tissue is made. In this embodiment, the bumper 17 comprises silicone material and extends about 1 to 2 mm from the edge of the substrate.

The top surface 101 of the substrate 10, which is configured to face towards the sclera in this embodiment, is curved both longitudinally and laterally. The degree of curvature in the lateral direction reduces as the substrate extends toward the distal end 11, as can be seen from a comparison of FIGS. 1b and 1c.

Figure 5A:
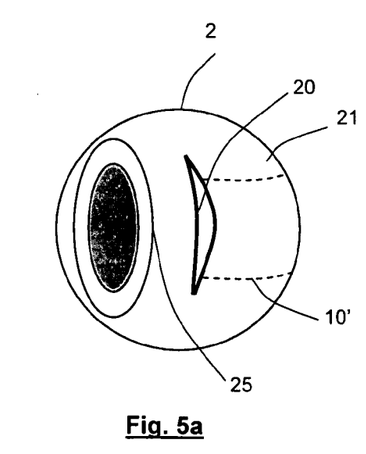
FIGS. 5a and 5b show side and rear views respectively of an eye having the prosthesis of FIG. 1a implanted therein.
Figure 5B:
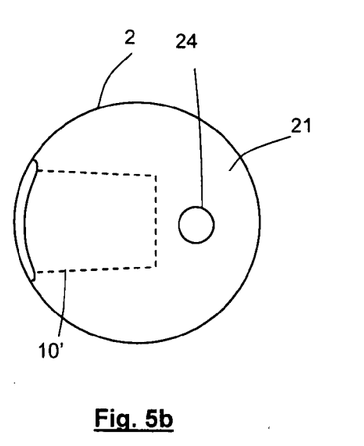

When the visual prosthesis 1 is fully implanted, the substrate 10 locates entirely between the sclera 21 and choroid 22. The electrodes 13 locate adjacent the active cells of the eye's retina 23, about 2 mm to 4 mm, e.g. 3 mm to one side of the optic disc 24 (see FIGS. 5a and 5b, in which the location of the substrate under the sclera is indicated by dotted lines 10'). Meanwhile, a region at the proximal end 12 of the substrate 10 sits over the incision 20 in the sclera 21.

The visual prosthesis 1 includes an anchor portion 18, formed of a relatively thin flap of material, connected to the proximal end 12 of the substrate. The anchor portion 18 is designed to extend into the incision 20, as shown in FIG. 2, and anchor the proximal end 12 of the substrate 10 thereto. Sutures used to close the incision 20 are also used to connect the anchor portion 18 to the tissue of the sclera 21. Accordingly, the proximal end 12 of the substrate 10 is substantially fixed in position relative to the sclera 21 whilst the distal end 11 of the substrate 'floats' between the sclera 21 and the choroid 22. Once fixed, part of the anchor portion 18 may be removed, reducing its size, enabling a greater area of scleral tissue either side of the incision 20 to rejoin. In alternative embodiments, the anchor portion comprises cut-out central sections to achieve a similar effect.

A cable 42 extends from the substrate, to connect the electrode interface to a wireless receiver located externally to the eye, as discussed further below. The cable 42 extends from the substrate at a similar position to the anchor portion 18 so that it can exit the eye through the incision 20. The cable 42 can also provide a form of anchor portion in addition to the anchor portion 18 discussed above.

The length of the substrate 10 between its distal and proximal ends 11, 12 is chosen to achieve the desired insertion arrangement. In this embodiment, the substrate is approximately 15 mm long from its connection with the anchor portion to the distal tip of the substrate, and the anchor portion is approximately 3 mm long (at least upon insertion). The substrate is approximately 8 mm wide.

The anchor portion 18 is connected to the substrate at a position about 1 to 3 mm, e.g. 2 mm, inwards from the proximal end edge 121. This leaves a proximal lip portion 19 of the substrate 10, positioned to the opposite side of the anchor portion 18 to the distal end 11 of the substrate 10. As can be seen in FIG. 2, the lip portion 19 ensures that the substrate 10 abuts the surface of the sclera 21 either side of the incision 20, ensuring that the anchor portion 18 is positioned in a balanced manner in the incision 20, and generally enhancing the stability of the device 1 and sealing of the incision at this region.

The visual prosthesis 1 forms part of a vision restoration apparatus. The apparatus includes an image receiver (e.g. a video camera) for receiving a stream of images, which may be positioned on eye glass frames; an image processor for converting the stream of images received by the image receiver into electrical signals, which may also be positioned on the eye glass frames; a wireless transmitter connected to the image processor for transmitting the electrical signals wirelessly, which may also be positioned on the eye glass frames; and a wireless receiver connected to the electrode interface unit for receiving the electrical signals from the wireless transmitter.

Figures 6, 8:
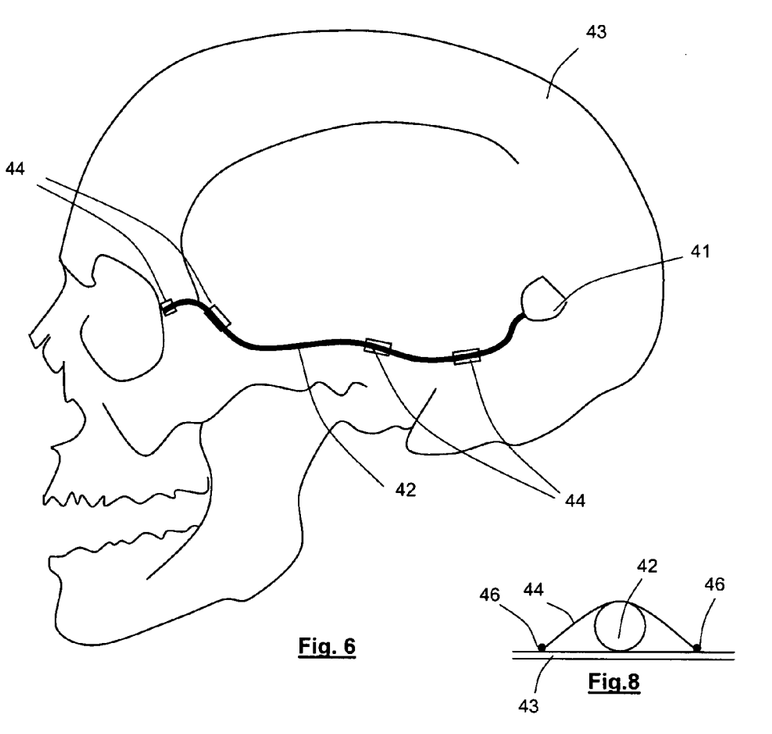
FIGS. 6 and 7 show the routing of a cable relative to the skull to connect the prosthesis of FIG. 1a to a wireless receiver.
FIG. 8 shows a cross-sectional view of the cable of FIGS. 6 and 7 anchored to a skull.
Figure 7:
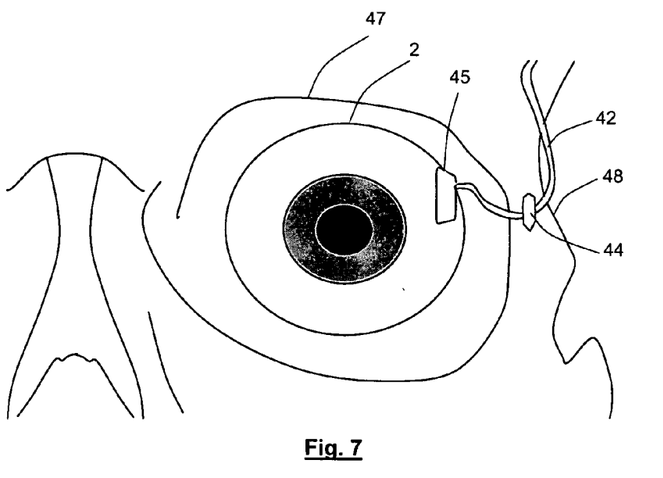

With reference to FIGS. 6 and 7, in the present embodiment, the wireless receiver 41 is implanted at the rear of the patient's head. The cable 42, which may be a helical cable with high flexibility, is connected between the wireless receiver 41 and the electrode interface unit 15. By having high flexibility, the cable 42 may be implanted relatively easily, and the cable 42 may flex as the eye 2 is rotated, without causing damaging to tissue as it exits the incision 20 in the sclera 21.

The cable 42 extends from the electrode interface unit 15, through the incision 20 in the sclera 21 and along the side of the user's skull 43 to the wireless receiver 41. To hold the cable 42 in position as it extends out of the incision 20 and along the side of the user's skull 43, a plurality of anchors 44, 45 are provided. The anchors 44 each comprise an open Dacron® mesh and extend over, and are adhered to, the cable 42, as shown in FIG. 8. Opposite sides of the anchors 44, 45 are fixed to the sclera/side of the user's head using sutures 46, e.g., Nylon 8.0 sutures. The anchors 44, 45 are Parylene coated with silicone to reduce adhesion between the anchors 44, 45 and body tissue. One of the anchors 45 is located adjacent the incision 20 in the sclera 21, ensuring that the cable 42 exits the incision 20 in a secure manner, preventing damage to the sclera 21 as the cable 42 flexes, e.g. due to rotation of the eye 2. The incision 20 and anchor 45 are strategically positioned on the sclera 21 to avoid interfering with the extraocular muscles. In this embodiment, the incision 20 is positioned in front of the connection between the eye and the lateral rectus muscle, and the anchor is configured to direct the cable rearward, over the top of the lateral rectus muscle and between the lateral rectus muscle and the superior rectus muscle.

In this embodiment, the cable 42 is provided with at least two different diameters as it extends between the electrode interface unit 15 and the wireless receiver 41. In particular, the cable 42 has a relatively small first diameter as it extends through the incision 20 in the sclera 21 allowing maximum closure of the incision after implantation to be achieved, and a relatively large second diameter as it extends onwards to the wireless receiver 41 providing the cable 42 with increased strength at this region. For example, the cable 42 may have the second diameter where it extends from the eye socket 47 around a relatively sharp turn to the temple region 48 of the skull 43. In this embodiment, the first diameter is between 0.2 and 1 mm, e.g., 0.64 mm, and the second diameter is between 1 mm and 2 mm, e.g., 1.19 mm. The cable 42 has the first diameter for about 30 mm of its length from its connection point with the electrode interface unit/substrate, and the second diameter for at least the next 30 mm of its length.

In alternative embodiments, the wireless receiver may be located on the surface of the eye (episclerally), rather than to the rear of the head.

Figure 9A:
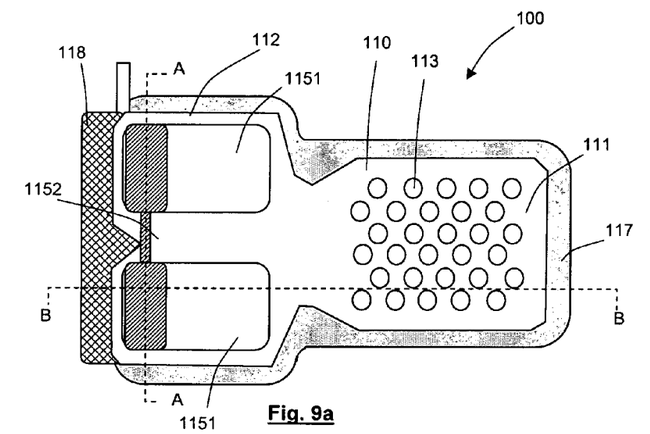
FIG. 9a shows a plan view of a prosthesis according to a second embodiment.
Figure 9B:
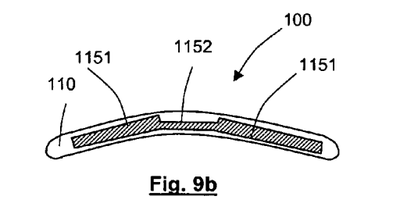
FIGS. 9b and 9c show cross-sectional views of the prosthesis along lines A-A and B-B of FIG. 9a respectively.
Figure 9C:
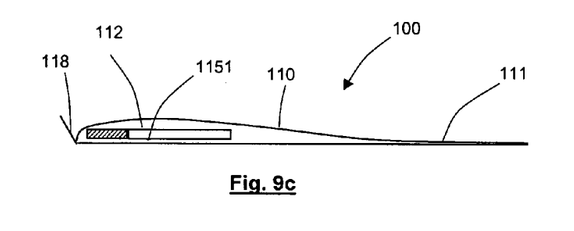

A visual prosthesis 100 according to a second embodiment is shown in FIGS. 9a to 9c. The prosthesis 100 has substantially the same configuration and functionality as the prosthesis 1 according to the first embodiment, including a substrate 110 extending between distal and proximal ends 111, 112, an electrode array 113 and a bumper 117. However, the proximal end 112 of the substrate in this embodiment is wider than the distal end 111. In this regard, the substrate 110 has a "T" shape when viewed from above (see FIG. 9a). This enables a larger electrode interface unit 115 to be used. In this embodiment, the electrode interface unit 115 actually comprises two cross point switch matrices 1151 that are spaced apart. By spacing the matrices apart, a central region 1152 between the two matrices 1151 can provide a bending point in the lateral direction of the substrate 110 (see FIG. 9b in particular), enabling the substrate to conform more closely to the anatomy of the sclera and choroid. Another difference over the first embodiment is the provision of the anchor portion 118 at the proximal end edge of the substrate 110.

A visual prosthesis 200 according to a third embodiment is shown in FIGS. 10a to 10d. Like the prosthesis 1 of the first embodiment, the prosthesis 200 includes an elongate substrate 210 extending between distal and proximal ends 211, 212, an electrode array 213, and a cable 242 connected to the electrode array 213.

In this embodiment, the prosthesis 200 does not comprise a dedicated anchor portion connected to the substrate. Rather, the prosthesis relies at least in part in the cable 242 extending through the scleral incision to provide an anchor portion, assisting in anchoring of the prosthesis 200 after insertion into the eye. A lip portion 219 (stabilising tail) of the substrate is provided to the proximal side of the connection point of the cable 242 and the substrate 210. The stabilising tail 219 ensures that the substrate abuts the surface of the sclera 21 either side of the incision 20 in which the cable 242 locates, enhancing the stability of the device at that region and improving sealing. The stabilizing tail 219 may be tucked into position after the distal end of the substrate has reached its stimulation position.

Figures 10A, 10B, 10C, 10D:
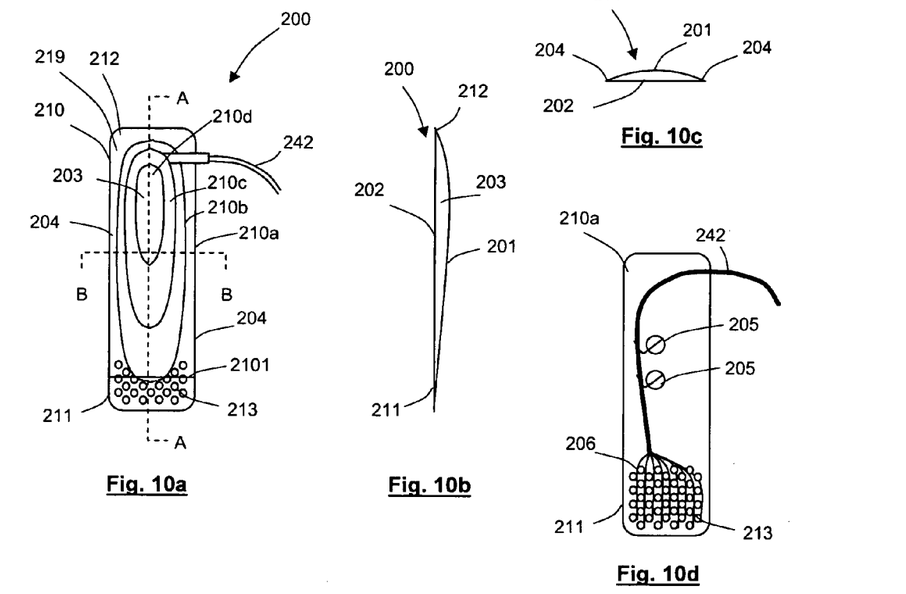

Prior to implantation, with reference to FIGS. 10b and 10c, the bottom surface 202 of the substrate 210, which is configured to face towards the choroid, is substantially flat and the top surface 201 of the substrate 210, which configured to face towards the sclera, is curved in both the longitudinal and lateral directions of the substrate 210. The substrate 210 is thickest at an intermediate region 203 between the distal and proximal ends 211, 212, the intermediate region 203 being closer to the proximal end 212 than the distal end 211. Accordingly, the substrate tapers in the longitudinal direction from the intermediate region 202 towards both the proximal end 212 and the distal end 211, but the length of the distal taper is greater than the proximal taper. Therefore, the substrate 210 is most flexible toward its distal end 212.

Referring to FIG. 10c, in the lateral direction, the top surface 201 has a part spherical profile that continues until it meets the bottom surface 202 at the lateral sides 204 of the substrate 210. Accordingly, in the lateral direction, the substrate 210 is more flexible towards the lateral sides 204.

The curved profile of the top surface 201, and the flexibility of the substrate 210, allows the substrate to conform substantially to the curved shapes of the choroid and scleral layers of the eye. Although the bottom surface 202 is flat prior to implantation, upon implantation, the substrate 210 can flex and the bottom surface 202 can take a curved configuration.

In this embodiment, the substrate is formed from four separately moulded layers 210a-210d that are bonded together to form a substrate 210 of laminar construction. The electrode array 213 is located on the bottom layer 210a. The layers 210a-210d have substantially the same thickness, but the dimensions of each layer in the lateral and longitudinal directions of the substrate become progressively smaller from the bottom layer 210a to the top layer 210d. Once the layers 210a-210d are bonded together, the edges of the layers 210a-210d may be rounded off to achieve a smooth, curved top surface 201. In alternative embodiments, the substrate may be formed from a single moulded element only, or via other methods.

With reference to FIG. 10d, which shows the bottom layer 210a only, it can be seen that an electrode interface unit is not provided in the substrate of the present embodiment. Instead, the electrode array 203, and two return electrodes 205, are each connected to electrical conductors 206, e.g., wires, which bundle together in the cable 242 and extend from the substrate to an electrode interface unit located remotely from the substrate 210 (not shown). The return electrodes 205 project from the bottom layer 210a of the substrate 210, and therefore an opening may be provided in at least the adjacent layer 210b of the substrate to accommodate the return electrodes 205.

With reference to FIG. 10a, when viewed from above, the substrate 210 is substantially rectangular, with curved corners, and the cable 242 extends from one side 204 of the substrate 210 adjacent the proximal end 211, in a direction substantially perpendicular to the longitudinal direction of the substrate. Accordingly, the substrate is configured for implantation to the lateral side of one eye (the right eye). Although not shown, a corresponding prosthesis for implantation via an incision on the lateral side of the opposite eye (the left eye) would have a cable extending substantially from the opposite side 204 of the substrate adjacent the proximal end 211.

Figure 12:
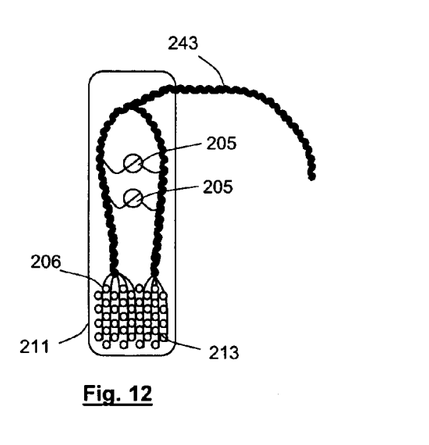

With reference to FIGS. 12 and 13, in certain embodiments, helical wiring may be employed to communicate electrically with the electrodes 213 in place of the flexible/lasered circuit lead shown in FIG. 10d, for example. The helical wiring can form part of a helical cable 243 extending from the substrate, as shown in FIG. 12, or it may also be helical in form as it extends internally within the substrate, as shown in FIG. 13. Coiling the wire and cable allows for stretching as the substrate flexes or the cable flexes, e.g., during insertion of the substrate in the eye or during subsequent use of the implanted substrate, e.g. when the eye rotates. The helical wire can be helical 25 µm platinum wire, for example.

Figure 11:
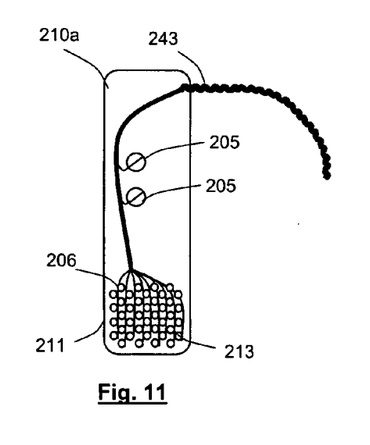
FIGS. 11 and 12 show top views of bottom layers of visual prostheses according to two further embodiments, the visual prostheses being similar to the visual prosthesis of FIG. 10a, but employing helical wiring.
Figure 13A:
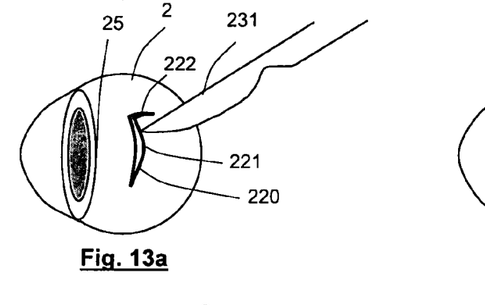
FIGS. 13a to 13d represent steps that can be carried out to implant the prostheses of FIGS. 10 to 12 in an eye.
Figure 13B:
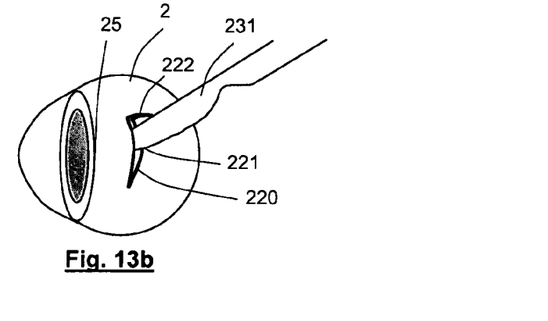
Figure 13C:
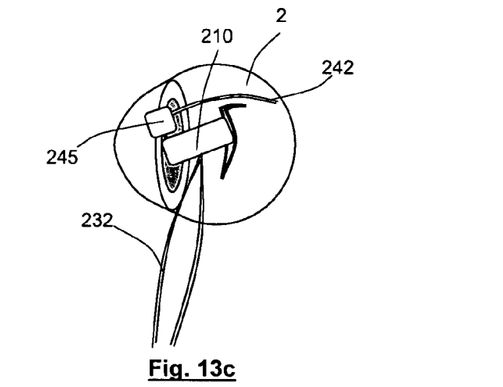

Implantation steps according to an embodiment of the invention, suitable for implanting the devices of FIGS. 10 to 12 in an eye, are represented in FIGS. 13a to 13d. An L-shaped incision 220 is made in the sclera with a scalpel 231, the L-shaped incision comprising a substantially vertical cut 221, and a substantially horizontal cut 222, in the surface of the sclera, the horizontal cut 222 extending rearward from the top of the vertical cut 221 (FIG. 13a). The vertical cut is slightly wider than the width of the substrate 210 and extends the full depth of the sclera at that point. After making the incision, a pocket is created between the sclera and the choroid using the scalpel 231 or further curved or crescent-shaped blade (FIG. 13b). The blade is extended through the incision and is manipulated in order to cleave the sclera and choroid apart. The pocket thus created extends from the end of the incision partway toward the stimulation position under the area centralis or macula. Using soft-tipped forceps 232, the distal end 211 of the substrate 210 is pushed through the vertical cut 221 and through the scleral layer into the pocket between the sclera and the choroid (FIG. 13c). A marker 2101 is provided on the top surface 201 of the substrate 210 to indicate when the substrate will have reached the end of the pocket. The pocket ensures that the substrate 210 is positioned in the appropriate anatomical plane between the sclera and choroid prior to further advancing of the distal end 211 of the substrate to the final stimulation position. After the distal end 211 reaches the stimulation position, the stabilizing tail 219 of the substrate is tucked into position between the sclera and choroid, to the opposite side of the incision to the distal end 211 of the substrate, ensuring that the entire substrate locates between the sclera and choroid and the substrate fits over the incision in a stable, sealed, manner.

Figure 13D:
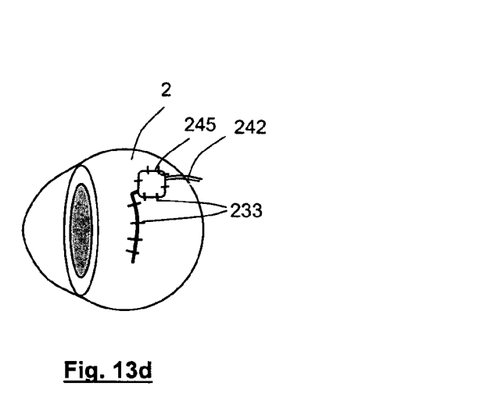

Due to the flexible, robust, construction of the substrate 210, the substrate can tunnel forward relatively easily through tissue and can be manipulated (e.g., turned) accurately to arrive at the stimulation position, while contact with the optic disc is avoided. During insertion, and once fully inserted, since the cable 242 extends from the substrate 210 substantially perpendicular to the longitudinal direction of the substrate, the cable 242 connected to the substrate 210 can extend through the horizontal cut 222, ensuring that the cable 242 does not obstruct insertion of the substrate 210 along a desired insertion path. After insertion, an anchor 245 connected to the cable 242 is fixed to the side of the eye 2 using sutures 233 to maintain the cable 242 in position. The opening of the incision 220 is then closed using sutures 233 (FIG. 13d). In this embodiment, the vertical cut of the incision 220 is about 5 mm from the corneal limbus 25.

Figure 14A:
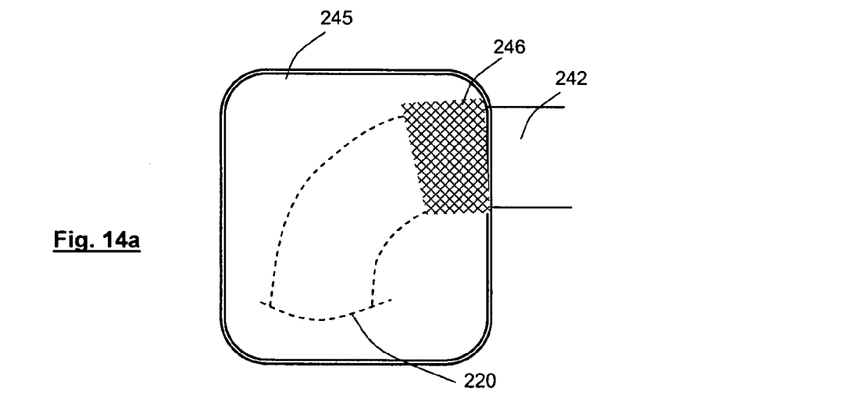
FIGS. 14a and 14b show top and side views, respectively, of a scleral patch for use with the prostheses of FIGS. 10 to 12.
Figure 14B:
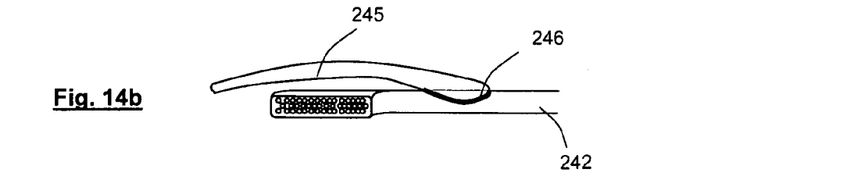

The anchor 245 is shown in more detail in FIGS. 14a and 14b. The anchor 245 takes the form of a substantially square patch 245. The patch 245 extends over the cable 242 at the incision 220 and is sutured to the sclera 2 to fix the cable 242 to the sclera 2. The path of the cable 242 underneath the patch is shown by dotted lines in FIG. 15a. As can be seen, as the cable 242 exits the incision 220, it extends in a substantially vertical direction. However, the patch 245 is configured to fix an approximately 90 degree bend in the cable 242 so that the cable extends from underneath the patch 245 in a substantially horizontal direction, towards the rear of the patient's skull. In this embodiment, the underside of the patch 245 is adhered to the cable 242 using glue 246 at one side of the patch only.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A visual prosthesis for implantation between a first tissue layer and a second tissue layer, comprising:
   a substrate having a distal end, a proximal end; and top and bottom surfaces extending in a longitudinal direction of the substrate between the distal end and proximal end; and
   an array of electrodes distributed across an electrode region of the substrate, the electrode region located adjacent the distal end of the substrate, the electrode region being defined by and between the outermost electrodes of the electrode array;
   wherein the distal end of the substrate is configured for insertion, via an incision, to a stimulation position between first and second tissue layers of an eye; and
   wherein, along the longitudinal direction, the thickness of the substrate between the top and bottom surfaces, including at the electrode region, tapers towards the distal end of the substrate.

2. The prosthesis of claim 1, wherein the first and second tissue layers are a sclera and a choroid of the eye and the distal end of the substrate is configured for insertion, via an incision in the sclera, to a position between the sclera and the choroid.

3. The prosthesis of claim 1, wherein, prior to insertion, at least one of a top and bottom surface of the substrate is substantially curved between the proximal and distal ends.

4. The prosthesis of claim 1, wherein the substrate has two opposite side edges extending between the distal and proximal ends and prior to insertion at least one of the top and bottom surface is substantially curved between the side edges.

5. The prosthesis of claim 4, wherein at least one of a top and bottom surface is substantially part-spherical between the side edges.

6. The prosthesis of claim 1, wherein:
   the substrate has two opposing side edges extending between the distal and proximal ends;
   the first and second tissue layers are a sclera and a choroid of the eye and the distal end of the substrate is configured for insertion, via an incision in the sclera, to a position between the sclera and the choroid;
   the top of the substrate is substantially curved between the distal and proximal ends;
   the top of the substrate is substantially part-spherical between the side edges; and
   the width of the substrate between the side edges is substantially uniform as the thickness of the substrate tapers toward the distal end.

7. The prosthesis of claim 1, wherein the tapering of the thickness of the substrate tapers towards the distal end of the substrate including at the electrode region starts from a region at or adjacent the proximal end of the substrate.

8. The prosthesis of claim 1, wherein along a central axis of the substrate that extends between the proximal and distal ends of the substrate at a position midway between opposing side edges of the substrate, the thickness of the substrate tapers towards the distal end of the substrate and a thickest region of the substrate along the central axis is located at an intermediate position between the distal end and the proximal end of the substrate.

9. The prosthesis of claim 8, wherein along the central axis the thickest region of the substrate is located closer to the proximal end of the substrate than the distal end of the substrate.

10. The prosthesis of claim 1, wherein, prior to insertion, the bottom surface of the substrate is a substantially flat surface.

11. The prosthesis of claim 1, wherein the distal end of the substrate is stiff enough to be pushed into the incision without buckling, yet flexible enough to at least substantially conform to the anatomy of the first and second tissue layers so that the substrate can be inserted without using a guide.

12. The prosthesis of claim 1, comprising one or more ribs or spines located in or on the substrate and extending along the longitudinal direction of the substrate at a position spaced from opposing side edges of the substrate.

13. The prosthesis of claim 1, comprising an electrode interface unit located in or on the substrate.

14. The prosthesis of claim 13, wherein the electrode interface unit is at or adjacent the proximal end of the substrate.

15. The prosthesis of claim 13, wherein the electrode interface unit is configured to locate between the first and second tissue layers after insertion of the distal end of the substrate to the stimulation position.

16. The prosthesis of claim 1 comprising an anchor portion connected to the substrate at or adjacent the proximal end of the substrate, wherein the anchor portion is configured to locate in the incision after insertion of the distal end of the substrate to the stimulation position.

17. The prosthesis of claim 1 comprising a non-flat cable, the cable extending outwardly from the substrate and providing a means for electrically communicating with at least one of the electrodes and/or an electrode interface unit, the cable being configured to extend through the incision when the distal end of the substrate is in the stimulation position.

18. The prosthesis of claim 16 comprising a non-flat cable, the cable extending outwardly from the substrate and providing a means for electrically communicating with at least one of the electrodes and/or an electrode interface unit, the cable being configured to extend through the incision when the distal end of the substrate is in the stimulation position, wherein the cable provides at least part of the anchor portion.

19. The prosthesis of claim 16, wherein the anchor portion comprises a substantially planar element comprising a mesh or one or more cut-out regions.

20. The prosthesis of claim 17, wherein the non-flat cable is connected to the substrate at a position spaced from a proximal end edge of the substrate.

21. The prosthesis of claim 20, wherein a region of the substrate extending from the non-flat cable to the proximal end edge of the substrate provides a stabilizing tail for the substrate, the stabilizing tail being configured to locate to the opposite side of the incision from the distal end of the substrate when the distal end of the substrate is located in the stimulation position.

22. The prosthesis of claim 1 comprising a bumper projecting from a distal end edge of the substrate.

23. The prosthesis of claim 22, comprising a bumper projecting from at least one of a proximal end edge and side edges of the substrate.

24. The prosthesis of claim 17, wherein the cable is a stretchable cable.

25. The prosthesis of claim 24, wherein the stretchable cable is a helical, twisted or curved cable.

26. The prosthesis of claim 17, wherein the cable is electrically connected to at least one of the electrodes and the electrode interface unit via stretchable wiring extending through the substrate.

27. The prosthesis of claim 26, wherein the stretchable wiring is helical, twisted or curved wiring.

28. The prosthesis of claim 1, comprising a patch and a non-flat cable, wherein
the cable extends outwardly from the substrate and provides a means for electrically communicating with the electrodes, the cable being configured to extend through the incision when the distal end of the substrate is in the stimulation position; and
the patch is configured for locating across at least a portion of the incision at the surface of the first tissue layer to support the cable as it exits the incision.

29. The prosthesis of claim 28, wherein the patch is configured to fix a bend in the cable upon exiting the incision.

30. The prosthesis of claim 28, wherein the patch is fixed to the cable during insertion of the substrate.

31. A device for implantation between a first tissue layer and a second tissue layer, comprising:
a substrate having a distal end, proximal end and top and bottom surfaces extending in a longitudinal direction of the substrate between the distal end and proximal end, and
an array of electrodes distributed across an electrode region of the substrate, the electrode region located adjacent the distal end of the substrate, the electrode region being defined by and between the outermost electrodes of the electrode array;
wherein the distal end of the substrate is configured for insertion, via an incision, to a stimulation position between first and second tissue layers; and
wherein, along the longitudinal direction, the thickness of the substrate between the top and bottom surfaces, including at the electrode region, tapers towards the distal end of the substrate.

32. A visual prosthesis for implantation between a first tissue layer and a second tissue layer, comprising:
a substrate having a distal end, a proximal end; a first side edge and an opposing second side edge, and top and bottom surfaces extending between the distal end and proximal end, the substrate having a central axis that extends between the proximal and distal ends at a position midway between the first and second side edges;
a plurality of electrodes located at or adjacent the distal end of the substrate;
wherein the substrate is configured for insertion, via an incision, to a stimulation position between first and second tissue layers of an eye; and
wherein, along the central axis, the thickness between the top and bottom surfaces tapers towards the distal end of the substrate from a position on the substrate that is closer to the proximal end of the substrate than the distal end of the substrate.

33. A visual prosthesis for implantation between a first tissue layer and a second tissue layer, comprising:
a substrate having a distal end, a proximal end, and top and bottom surfaces extending between the distal end and proximal end in a longitudinal direction of the substrate;
a plurality of electrodes located at or adjacent the distal end of the substrate;
wherein the substrate is configured for insertion, via an incision, to a stimulation position between first and second tissue layers of an eye;

wherein the prosthesis further comprises a non-flat cable, the cable connected to and extending outwardly from the substrate at a position that is spaced from the proximal end of the substrate and closer to the proximal end of the substrate than the distal end of the substrate, the cable being configured to extend through the incision when the distal end of the substrate is in the stimulation position of the substrate and providing for electrical connection with at least one of the electrodes; and wherein the thickness between the top and bottom surfaces tapers towards the distal end of the substrate from a position on the substrate that is closer to the proximal end of the substrate than the distal end of the substrate.

34. The visual prosthesis of claim 32, wherein the non-flat cable includes a round cable.

35. The visual prosthesis of claim 32, wherein the non-flat cable is substantially circular in cross-section.

* * * * *